United States Patent [19]

Ford

[11] Patent Number: 5,779,674
[45] Date of Patent: Jul. 14, 1998

[54] FLUID GAS REMOVAL DRIP CHAMBER

[75] Inventor: Steven Ford, Woods Cross, Utah

[73] Assignee: Mallinckrodt Medical, Inc., St. Louis, Mo.

[21] Appl. No.: 642,955

[22] Filed: May 6, 1996

[51] Int. Cl.⁶ ........................................ A61M 5/14
[52] U.S. Cl. .................. 604/126; 604/251; 604/252; 604/122
[58] Field of Search .................. 604/122, 126, 604/167, 251, 252, 254, 255, 403, 407, 80–85

[56] References Cited

U.S. PATENT DOCUMENTS

| | | |
|---|---|---|
| 3,776,229 | 12/1973 | McPhee . |
| 3,778,971 | 12/1973 | Granger et al. ............... 55/159 |
| 3,854,907 | 12/1974 | Rising ............................ 55/159 |
| 3,993,062 | 11/1976 | Jess ............................ 128/214 R |
| 4,013,072 | 3/1977 | Jess ............................ 128/214 C |
| 4,031,891 | 6/1977 | Jess ............................ 128/214 R |
| 4,223,695 | 9/1980 | Muetterties ................... 137/173 |
| 4,278,084 | 7/1981 | Pope, Jr. .................... 128/214 R |
| 4,298,358 | 11/1981 | Ruschke ........................ 55/185 |
| 4,326,957 | 4/1982 | Rosenberg .................... 210/436 |
| 4,332,247 | 6/1982 | Mittleman et al. . |
| 4,521,211 | 6/1985 | Theeuwes ....................... 604/85 |
| 4,568,366 | 2/1986 | Frederick et al. ............. 55/159 |
| 4,571,244 | 2/1986 | Knighton ...................... 604/118 |
| 4,572,724 | 2/1986 | Rosenberg et al. ............ 55/159 |
| 4,615,694 | 10/1986 | Raines ......................... 604/126 |
| 4,662,906 | 5/1987 | Matkovich et al. ............ 55/159 |
| 4,743,243 | 5/1988 | Vaillancourt ................. 604/411 |
| 4,750,643 | 6/1988 | Wortrich ...................... 604/411 |
| 4,900,308 | 2/1990 | Verkaart ...................... 604/126 |
| 5,045,096 | 9/1991 | Quang et al. .................. 55/159 |
| 5,126,054 | 6/1992 | Matkovich .................... 210/641 |
| 5,242,424 | 9/1993 | Chen ........................... 604/251 |

FOREIGN PATENT DOCUMENTS

| | | |
|---|---|---|
| 62913 | 10/1982 | European Pat. Off. . |
| 1077115 | 11/1954 | France . |

Primary Examiner—John G. Weiss
Assistant Examiner—David J. Cho
Attorney, Agent, or Firm—Madson & Metcalf

[57] ABSTRACT

A fluid gas removal drip chamber for use for parenteral administration of fluids is disclosed. The drip chamber has a hydrophobic barrier which extends into the interior of the drip chamber. The hydrophobic barrier preferably comprises at least a portion of a three-dimensional surface. In one embodiment, an inlet port allows fluid to enter the drip chamber from the top so that the fluid falls through an air space formed in the top of the drip chamber. By shaping the inlet port so that droplets of fluid are formed, a health care professional can monitor the fluid drip rate. In another embodiment, the hydrophobic barrier is configured so that little or no air space exists at the top of the drip chamber. The drip chamber includes means for venting air that is separated from the fluid within the chamber and, at the same time, preventing air from entering the chamber through the venting means. For certain applications, the drip chamber is provided with a hydrophilic filter for filtering the fluid prior to exiting the drip chamber.

22 Claims, 7 Drawing Sheets

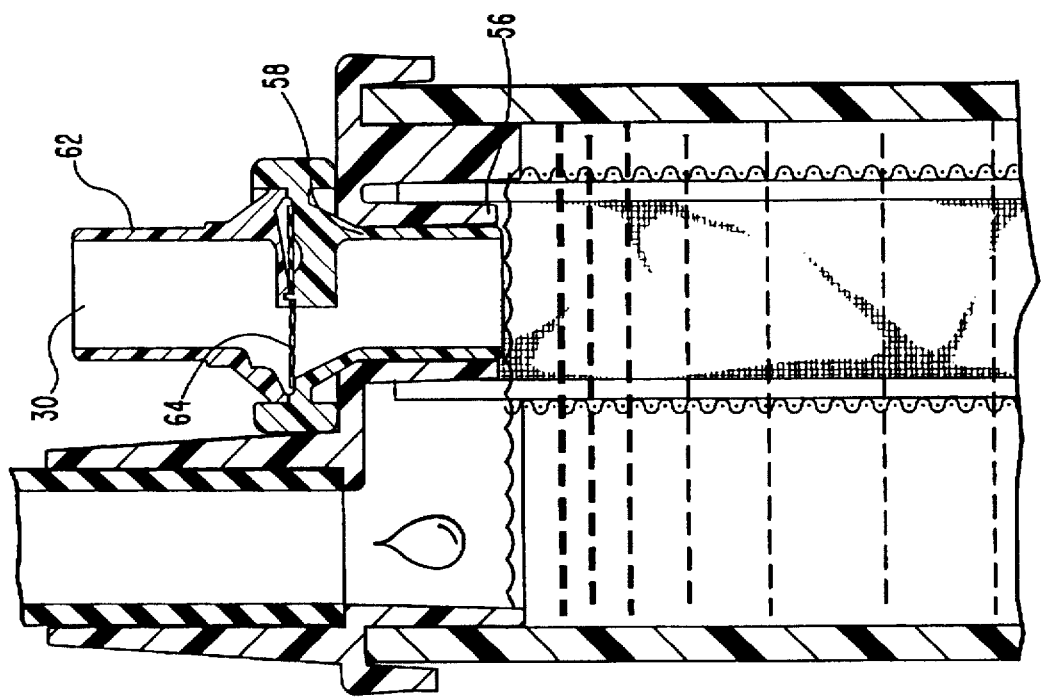
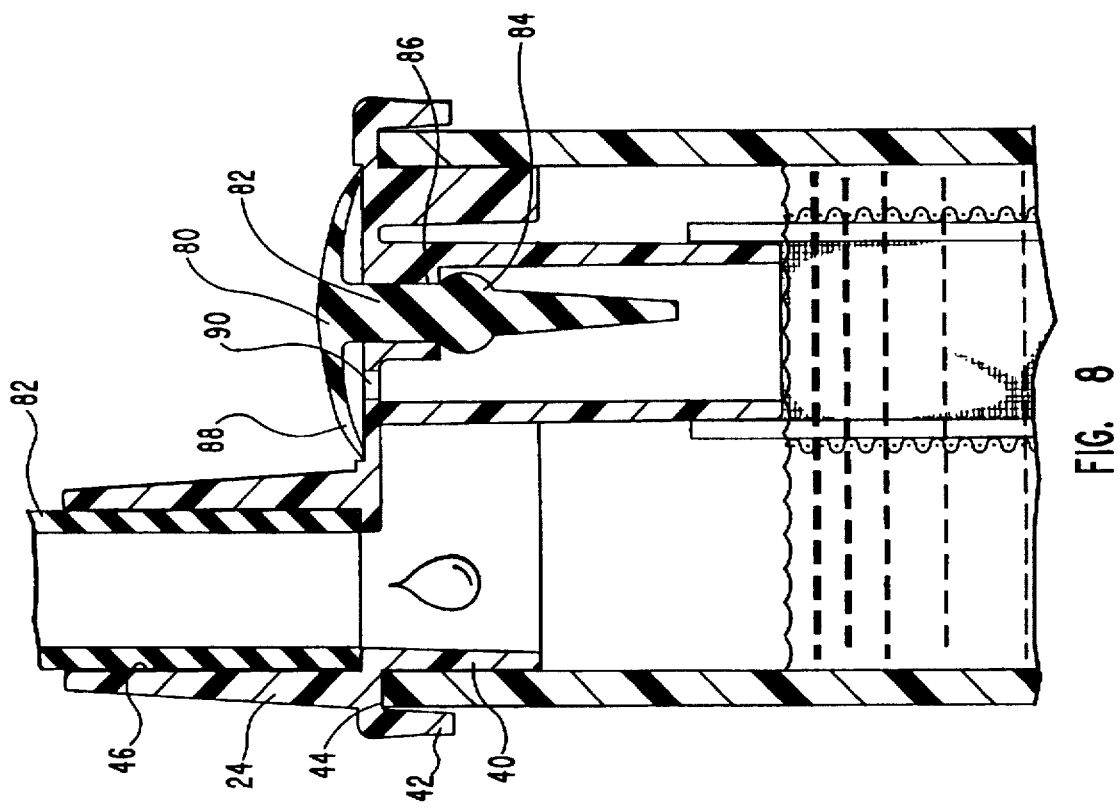

FLUID GAS REMOVAL DRIP CHAMBER

BACKGROUND OF THE INVENTION

1. The Field of the Invention

This invention relates to a device for removing gas from solutions for parenteral administration to a patient, and, in particular, to a drip chamber for removing gas from liquids prior to parenteral infusion into a patient.

2. Present State of the Art

In modern medicine a wide variety of fluids are administered parenterally. Such fluids can include blood, plasma, a standard saline solution or other fluid. Prior to infusion of any fluid, however, it is generally desired to remove air or other gases which might be present in the solution. In many situations, removal of gas is absolutely essential to avoid a gas embolism.

To accomplish this function, a wide variety of devices have been developed that are capable of removing gas or air suspended or entrained in the fluid. Most devices employ some sort of chamber with a fluid inlet and a fluid outlet. The devices may contain various filtering elements and passages to vent removed gas outside the chamber.

In some devices, the chamber is used to collect gas that has been extracted from the liquid flowing through the chamber. The gas is then vented outside the chamber through a hydrophobic membrane or filter. A hydrophobic membrane permits gas to pass therethrough, but is resistant to the passage of liquid. Since gas naturally rises to the top of the chamber, many devices locate the hydrophobic filter at the top of the chamber. The fluid inlet is generally located below the hydrophobic filter. This allows the gas extracted from the fluid to rise to the top of the chamber and be vented through the hydrophobic filter.

While this arrangement of fluid inlet and hydrophobic filter seems naturally to compliment the physical characteristics of the liquid and gas, it also creates several problems. For example, in most devices there is no way to estimate the flow rate of the fluid through the chamber. Thus, in applications where it is desirable to visually estimate the flow rate of the fluid through the chamber, some other device must also be located in fluid communication with the chamber. For example, a separate drip chamber may be located in line with the gas removal chamber. By watching the drip rate in the drip chamber a health care professional can estimate the flow rate of the fluid. Unfortunately, it is not often convenient to locate a drip chamber in line with the gas removal chamber. An extra drip chamber adds additional expense and complexity to the setup.

Collection of air inside the drip chamber is another problem when a separate drip chamber is used. A drip chamber must contain an air space so that a health care professional can watch the fluid drip. Because many drip chambers are not automatically vented, if extra air collects in the drip chamber air space, it may be forced out of the drip chamber into the fluid line. Thus, in many cases, use of a drip chamber requires close monitoring by health care professionals. This is often an undesirable result. Thus, no device currently exists which satisfactorily addresses the problem of estimating fluid flow rate through a fluid gas removal chamber.

Not wishing to be bound by theory, it is also presently believed that hydrophobic filters which are horizontally positioned in the top of the chamber become unintentionally "clogged" when the fluid level reaches the membrane and then drops below the membrane. This "clogging" is caused by fluid which adheres to the horizontal membrane surface due to fluid surface tension effects. Air cannot pass through the membrane with fluid adhering to the membrane surface, effectively "clogging" the membrane.

Finally, current gas removal devices are sometimes incapable of handling a large volume of air which is introduced into the chamber along with the liquid. For example, hydrophobic filters located in the upper portion of the gas removal chamber by necessity have a fixed cross section. The cross sectional area of the hydrophobic filter, along with the degree of clogging which has taken place, affect the maximum flow rate of air through the hydrophobic filter. If, therefore, a large volume of air is suddenly introduced into the chamber, the maximum flow rate of the filter will determine how long it takes to vent the air to the outside. If the flow rate is not large enough to handle repeated introduction of large volumes of air into the chamber, the chamber will completely fill with air and become useless. Thus, it would represent an advancement in the art to construct a filter which could accommodate a high flow rate of air through the hydrophobic filter so that the chamber functions normally even in the presence of repeated volumes of air introduced into the chamber.

SUMMARY OF THE INVENTION

The present invention is directed to a fluid gas removal drip chamber having a hydrophobic barrier which extends into the interior of the drip chamber. The hydrophobic barrier preferably comprises at least a portion of a three-dimensional surface. An inlet port allows fluid to enter the drip chamber from the top so that the fluid falls through an air space formed in the top of the drip chamber. By shaping the inlet port so that droplets of fluid are formed, a health care professional can estimate the flow rate of the fluid by watching the drip rate as the fluid falls through the air space in the top of the drip chamber.

Because the hydrophobic barrier extends into the drip chamber, when fluid fills the chamber the hydrophobic barrier will be submerged in the fluid. Liquid will not flow through the hydrophobic membrane. As entrained gas separates from the liquid, the gas rises to the top of the chamber and collects in the air space. As the air space increases, it forces the fluid level down slightly to expose a portion of the hydrophobic membrane. The air then passes through the exposed hydrophobic membrane and is vented outside the chamber. Thus, the surface area of the hydrophobic membrane varies according to the amount of air collected in the top of the drip chamber. When a large volume of air is introduced into the drip chamber, it forces the fluid level down to a greater extent and exposes a larger surface area of the hydrophobic membrane.

Because the hydrophobic membrane extends into the chamber, at least a portion of the hydrophobic membrane is submerged in the liquid. The submerged portion of the hydrophobic membrane is not used to vent gas from the chamber until it is exposed as previously described. If large amounts of entrained air are introduced into the chamber, the air collected in the top of the chamber forces the fluid level down to expose sufficient surface area of hydrophobic filter needed to pass air therethrough.

Other preferred embodiments of the instant invention contain a screen or hydrophilic filter located between the fluid inlet and the fluid outlet of the drip chamber. The screen or hydrophilic filter is used in some applications to provide further filtering of the fluid prior to parenteral infusion into a patient. When a hydrophilic filter is used, the filter can also help prevent passage of air through the drip chamber fluid outlet. A hydrophilic filter, once wetted, will readily pass liquid but will inhibit passage of air.

Still other embodiments of the inventive fluid gas removal chamber contain an umbrella valve or check valve in fluid communication with the hydrophobic filter in order to prevent vented gas from re-entering the drip chamber.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawing depict only typical embodiments of the invention and are therefore not to be considered to be limiting of its scope, the invention in its presently understood best mode for making and using the same will be described with additional specificity and detail through the use of the accompanying drawings in which:

FIG. 8 is an enlarged cross sectional view of the proximal end of the fluid gas removal chamber illustrated in FIG. 4; and FIG. 9 is an enlarged cross sectional view of the proximal end of the fluid gas removal chamber illustrated in FIG. 5.

DETAILED DESCRIPTION OF THE INVENTION

Figure 1:
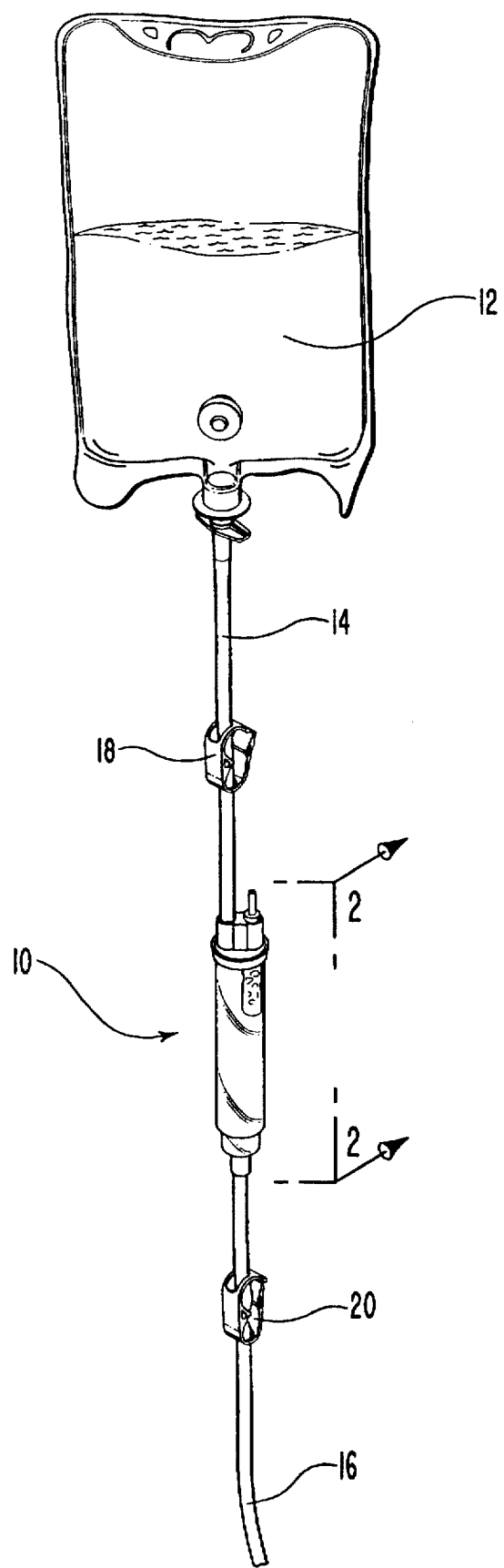
FIG. 1 is a perspective view illustrating a system incorporating one embodiment of the fluid gas removal chamber of the present invention.

Referring to FIG. 1, one presently preferred embodiment of the fluid gas removal drip chamber of the present invention, generally designated 10, is illustrated as part of a system for parenterally administering fluids comprising a media bag 12, inlet line 14, drip chamber 10 and outlet line 16. The flow of liquid from media bag through inlet line 14 can be selectively blocked by the use of a tubing clamp 18. Similarly, the flow of fluid out of drip chamber 10 and through outlet line 16 can be selectively controlled through the use of tubing clamp 20.

The structure of one embodiment of the inventive fluid gas removal drip chamber will now be described with reference to FIGS. 2–3. In the following description, when the term "proximal end" is used to describe a component of drip chamber 10, it will refer to the end of that component that is situated closest to or oriented toward media bag 12. Similarly, when the term "distal end" is used to described a component of drip chamber 10, it will refer to that end of the component that is closest to or oriented toward outlet line 16.

Drip chamber 10 comprises an elongated, tubular housing 22 and an end cap 24. Together, housing 22 and end cap 24 define an interior chamber 26 for receiving and collecting fluids. Drip chamber 10 further comprises an elongated, cylindrically shaped hydrophobic filter assembly 28 and a check valve 30. As best illustrated in FIG. 2, housing 22 has a generally elongated, tubular shape. In the presently preferred embodiment, housing 22 has a first portion 32 of substantially uniform diameter, an intermediate cylindrical portion 34 having a slightly reduced diameter, a conically shaped portion 36 and an outlet nipple 38. Outlet nipple 38 is configured to receive the proximal end of outlet line 16 in mating relationship. The proximal end of outlet line 16 is permanently and securely fastened to the inner wall of outlet nipple 38 through the use of a suitable adhesive. The precise dimensions of housing 22 depend on the desired volume, the presently preferred range for which is 5–35 milliliters, as well as the desired medical application for which the drip chamber 10 is to be utilized.

The distal end of end cap 24 is configured to receive the proximal end of housing 22 in mating relationship. As shown in FIG. 2, the proximal end of end cap 24 includes an inner annular flange 40 and an outer annular flange 42. Together flanges 40 and 42 form an annular recess 44 around the periphery of the distal end of end cap 24, which receives the proximal end of housing 22 in mating relationship. The proximal end of housing 22 is securely and permanently fastened within recess 44 through the use of a suitable adhesive. Cap 24 also has a throughbore 46 that is configured to receive the distal end of inlet line 14 in mating relationship. The distal end of inlet line 14 is securely and permanently fastened within throughbore 46 through the use of suitable adhesive. End cap 24 further comprises an interior recess 48, which is configured to house check valve 30 and to receive the proximal end of hydrophobic filter assembly 28. End cap 24 is preferably made of rigid PVC, but could also be made of rigid or semi-rigid polycarbonate, ABS or other suitable material.

Drip chamber 10 includes a means for delivering fluid to interior chamber 26. In one presently preferred embodiment, the fluid delivery means simply comprises inlet line 14, which extends through end cap 24 and terminates at the proximal end of interior chamber 26. Optionally, inlet line 14 may also terminate in a nozzle (not shown) that is designed to form the fluid delivered through inlet line 14 into droplets before falling into interior chamber 26.

Drip chamber 10 also comprises a barrier means, disposed adjacent the top end and extending into interior chamber 26, for establishing a vertically dimensional hydrophobic barrier that will allow air to pass from interior chamber 26, without passing fluid. In one presently preferred embodiment, the barrier means comprises a hydrophobic filter assembly 28. As best illustrated in FIG. 3, hydrophobic filter assembly 28 comprises a cylindrical hub 50, a hydrophobic membrane 52, and a support structure 53 that is disposed within membrane 52. At least a portion of the hydrophobic membrane 52 forms a three-dimensional surface around the support structure 53. As used herein, a three-dimensional surface means a surface that is not planar. A portion of hub 50 is configured to mate within interior recess 48 of end cap 24. As best shown in FIGS. 2 and 3, hub 50 also includes a throughbore 56, which is configured to receive the distal end of check valve 30 in mating relationship. Hub 50 is permanently and securely fastened within interior recess 48, and the distal end of check valve 30 is securely and permanently secured to the inner wall of throughbore 56, by means of a suitable adhesive material.

While a variety of hydrophobic membranes are commercially available, in the presently preferred embodiment, membrane 52 is made out of a membrane material from Gelman Sciences under the trademark VERSAPOR™, having an average pore size of 0.45 microns. Other hydrophobic membranes are commercially available, such as a membrane material available from W. L. Gore having a pore size of 1 micron with a non-woven backing and teflon coating on one surface. Suitable hydrophobic membranes may also be considered "oleophobic" in the art.

Figure 3:
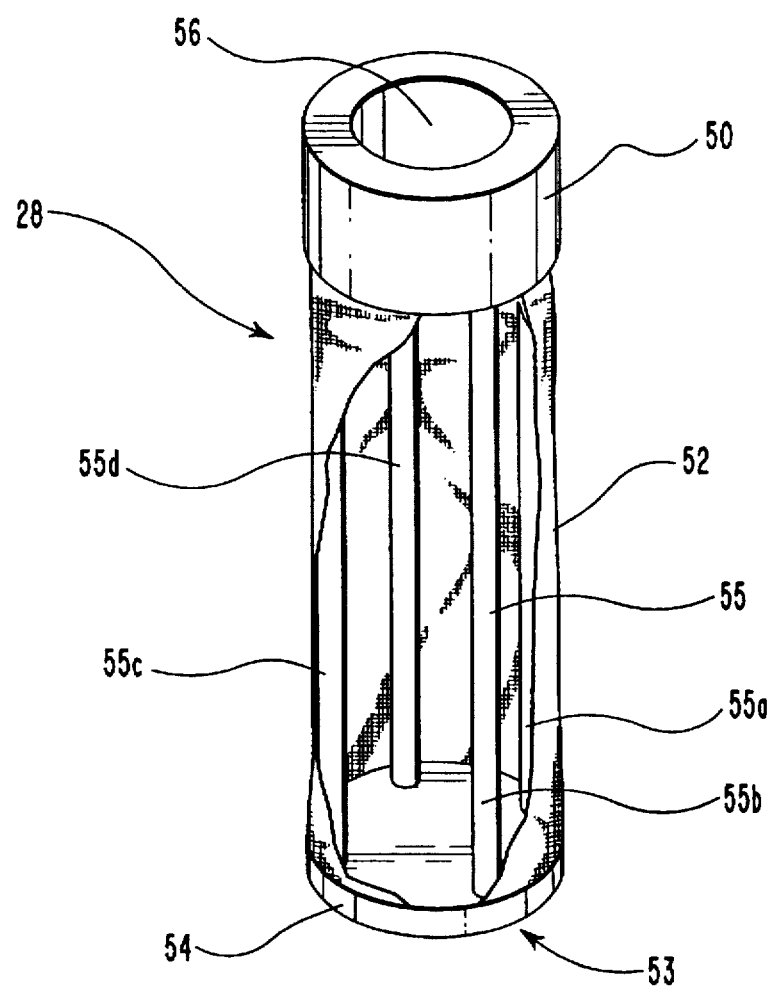
FIG. 3 is an enlarged perspective view of one embodiment of the hydrophobic filter.

Support structure 53 shown in FIG. 3 is composed of a circular disk 54 situated at the distal end of membrane 52. Interposed between and integrally attached to hub 50 and circular disk 54 are four elongated ribs 55a-d, which are radially spaced at 90° intervals about the periphery of filter assembly 28. Support structure 53 provides structural support to membrane 52, thereby preventing membrane 52 from collapsing under the force of fluid and/or gas pressures generated within interior chamber 26. Support structure 53 can be made rigid or semi-rigid nylon, ABS, polycarbonate or other suitable material. Alternatively, support structure 53 can take the form of a cylinder made out of rigid or semi-rigid open cell foam and configured to fit within membrane 52.

Figure 2:
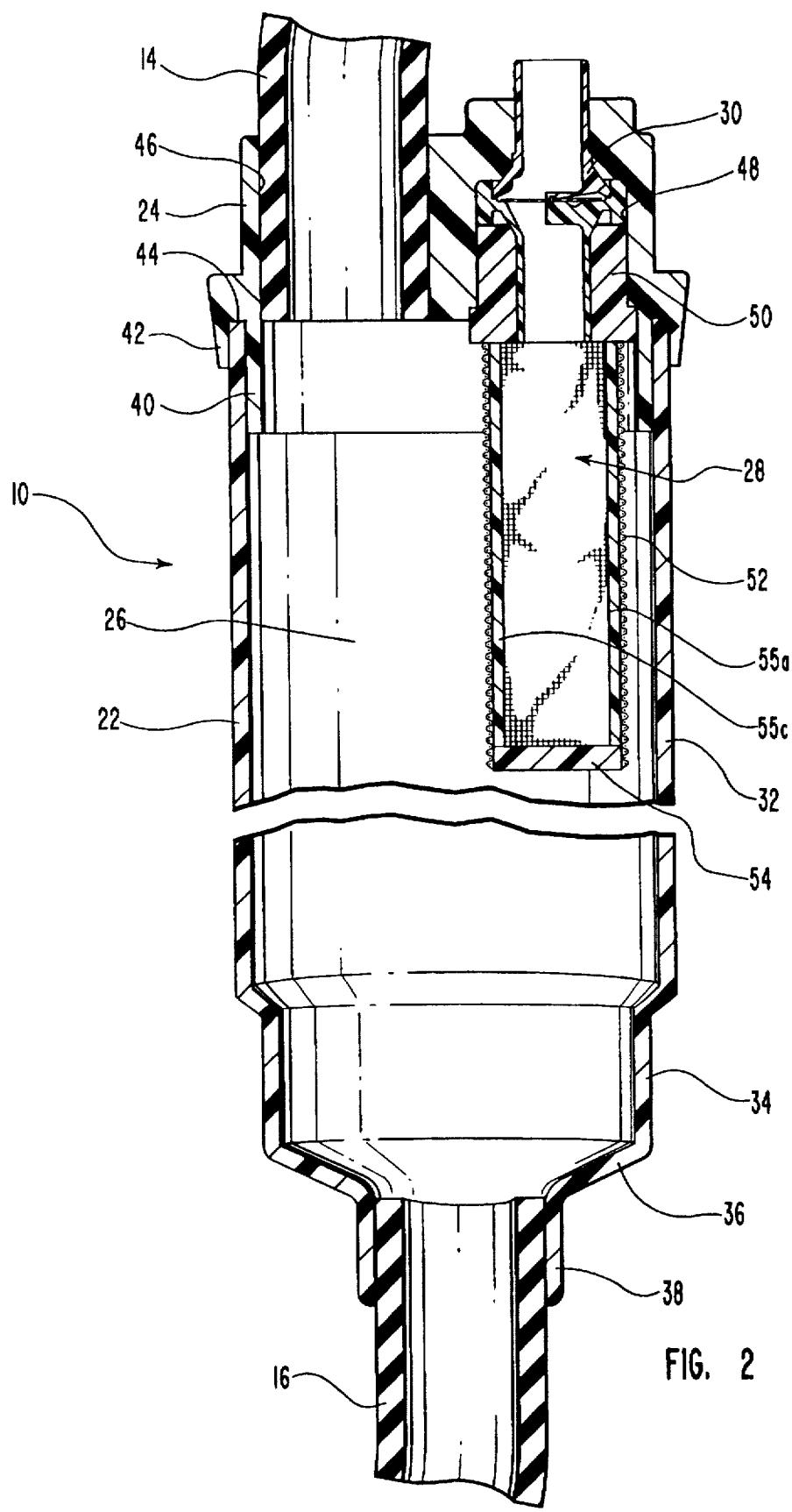
FIG. 2 is a cross sectional view taken along line 2—2 in FIG. 1 further illustrating the embodiment of the inventive fluid gas removal chamber.

As best shown in FIG. 2, with hub 50 situated within interior recess 48, the proximal end of hydrophobic membrane 52 is positioned adjacent, but slightly lower than the distal end of inlet tube 14. As will be discussed in more detail below, during the use of drip chamber 10, air is trapped in the space between the distal end of inlet tube 14 and the proximal end of membrane 52, thereby providing a visual means for measuring the flow rate of fluid through inlet tube 14 and entering interior chamber 26 of drip chamber 10. The height or size of the head space at the top of interior chamber 26 can be increased or decreased by increasing or decreasing the dimension of hub 50 along its longitudinal axis. In those embodiments where visual monitoring of the flow rate is desired, then the proximal end of membrane 52 is spaced sufficiently below the top of interior chamber 26. In other embodiments where flow rate is not monitored, the head space can be eliminated, thereby reducing the size and material costs for the chamber.

Drip chamber 10 further comprises a vent means for venting air that has passed from interior chamber 26 through hydrophobic membrane 52 to the atmosphere and, at the same time, prevents the passage of air from the atmosphere into drip chamber 10. In one presently preferred embodiment, the vent means comprises a check valve 30. As illustrated in FIG. 2, check valve 30 comprises an inlet tube 58, an enlarged center hub 60, and an outlet tube 62. Disposed within center hub 60 is diaphragm 64, which permits passage of air through the inlet tube 58 and outlet tube 62 in FIG. 2, but prevents airflow in the opposite direction. Check valve 30 provides a passage extending from the interior of hydrophobic filter assembly 28 to the outside atmosphere, thereby providing means for venting air introduced into interior chamber 26 to the atmosphere, while at the same time, providing a means for preventing air from entering interior chamber 26 through check valve 30.

Check valve has a relatively low pressure break point, preferably in the range of 1–2 psi, with respect to air pressure build up within interior chamber 26 so that check valve 30 readily vents to the atmosphere air that is separated from the fluid contained within interior chamber 26.

While a variety of suitable check valves are commercially available, in one presently preferred embodiment of the invention, check valve 30 is a product manufactured by The Filtertek Companies and marketed under the product name CenterPost Surevalve. Another commercially available check valve is manufactured by Burron Medical.

Figure 6:
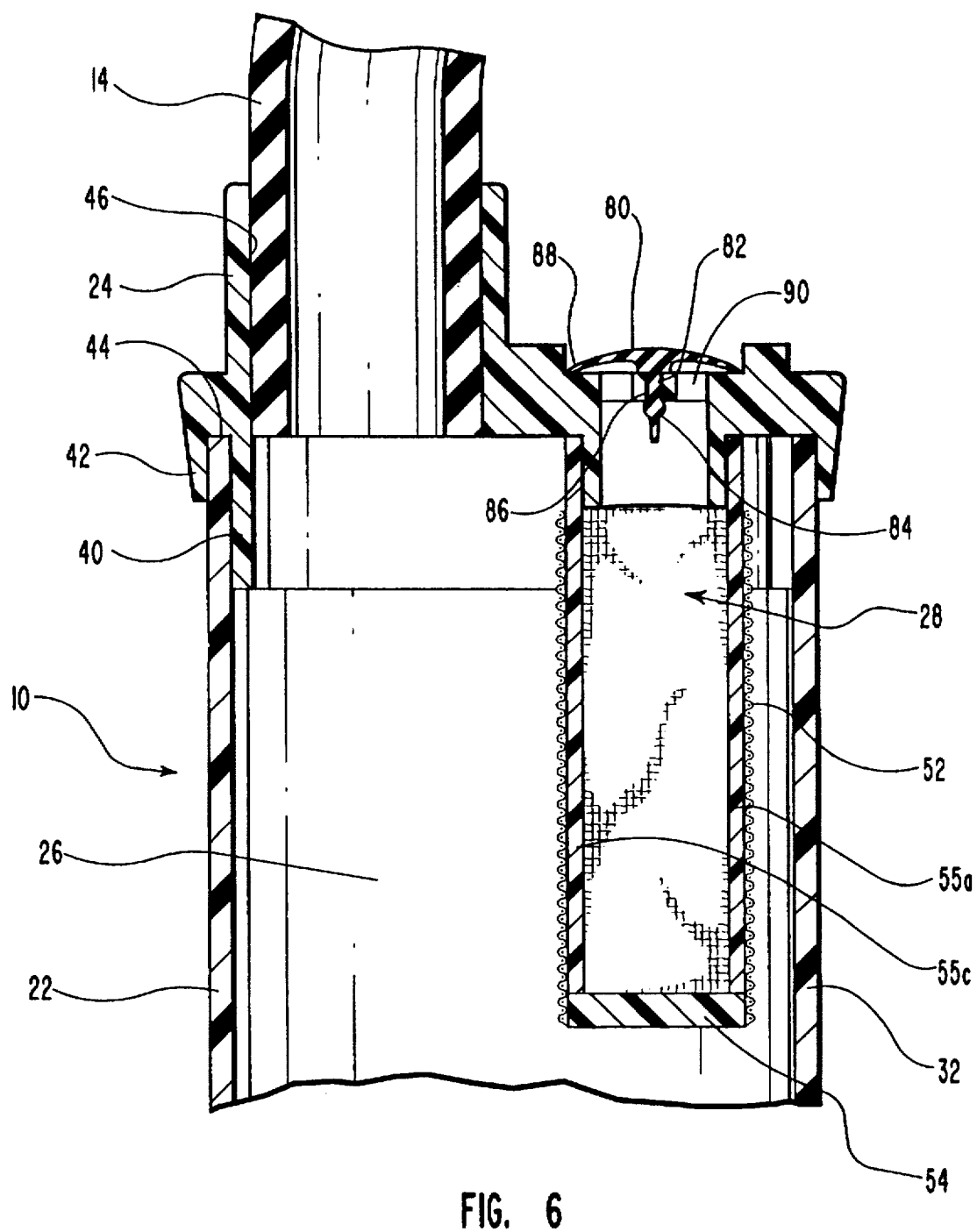
FIG. 6 is a cross sectional view of yet another fluid gas removal chamber within the scope of the present invention having an umbrella valve instead of a check valve.
Figure 7:
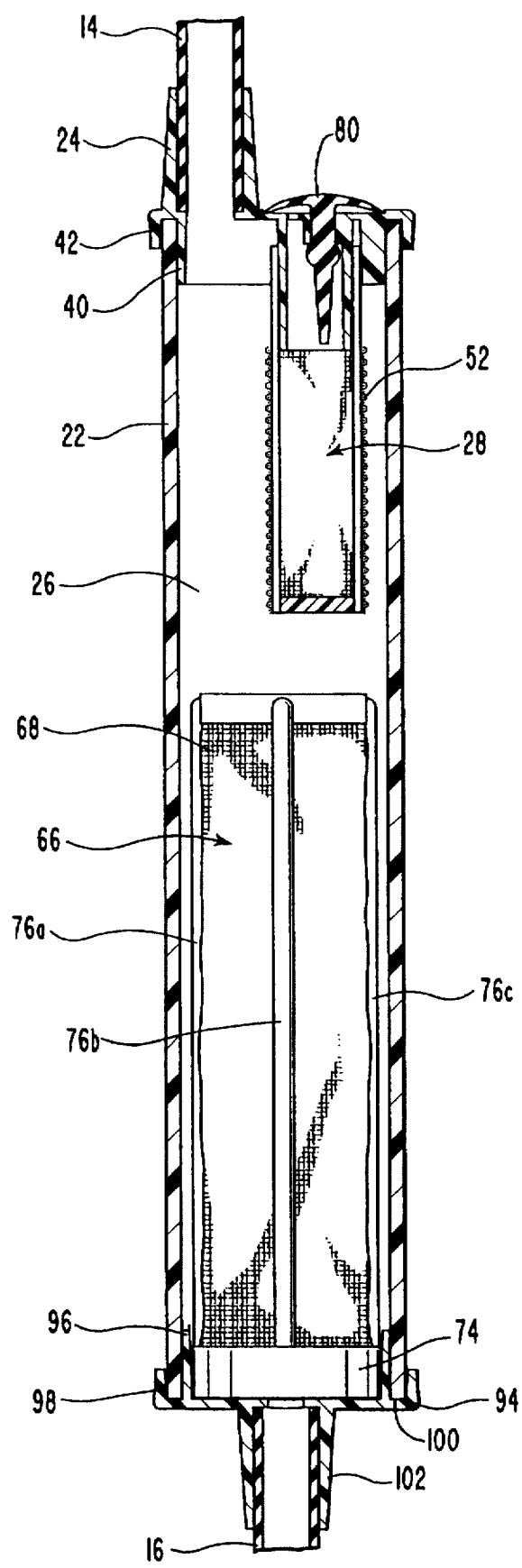
FIG. 7 is a cross sectional view of another fluid gas removal chamber within the scope of the present invention in which the tubular housing has caps at both the proximal and distal ends.

Another vent means for venting air from the interior chamber 26 through hydrophobic membrane 52 to the atmosphere and preventing exterior air from entering the drip chamber is an umbrella valve 80, illustrated in FIGS. 4, 6, 7 and 8. The umbrella valve 80 is preferably constructed of a flexible, polymeric material, such as silicone or polyurethane. Suitable umbrella valves are commercially available from Vernay Laboratories. As shown in FIG. 7, the umbrella valve 80 is used with a modified cap 24. The umbrella valve has a stem 82 having a rounded bulb 84 at one end thereof. The stem 82 and bulb 84 are pressed through an opening 86 in cap 24. The bulb 84 helps keep the umbrella valve 80 positioned close to the cap 24 so that the valve periphery 88 seals against cap 24. Vents 90, molded into cap 24, allow air to flow from the interior of the hydrophobic filter assembly 28, through the umbrella valve 80, to the outside atmosphere.

The proximal end of the hydrophobic filter assembly 28 shown in FIG. 6 extends to the top of the interior chamber 26 such that it is approximately level with the distal end of inlet tube 14. In this embodiment, the drip chamber 10 will fill substantially entirely with fluid. As mentioned above, and illustrated in FIGS. 8 and 9, the proximal end of the hydrophobic filter assembly 28 may be positioned at any distance from the top of the interior chamber 26 to provide fluid level control. With the filter assembly 28 positioned at the top of interior chamber 26 so that their is no head space, the drip chamber 10 can be reduced in size. Such an embodiment is preferably used in combination with a commercially available drip chamber for measurement of flow rate.

Figure 4:
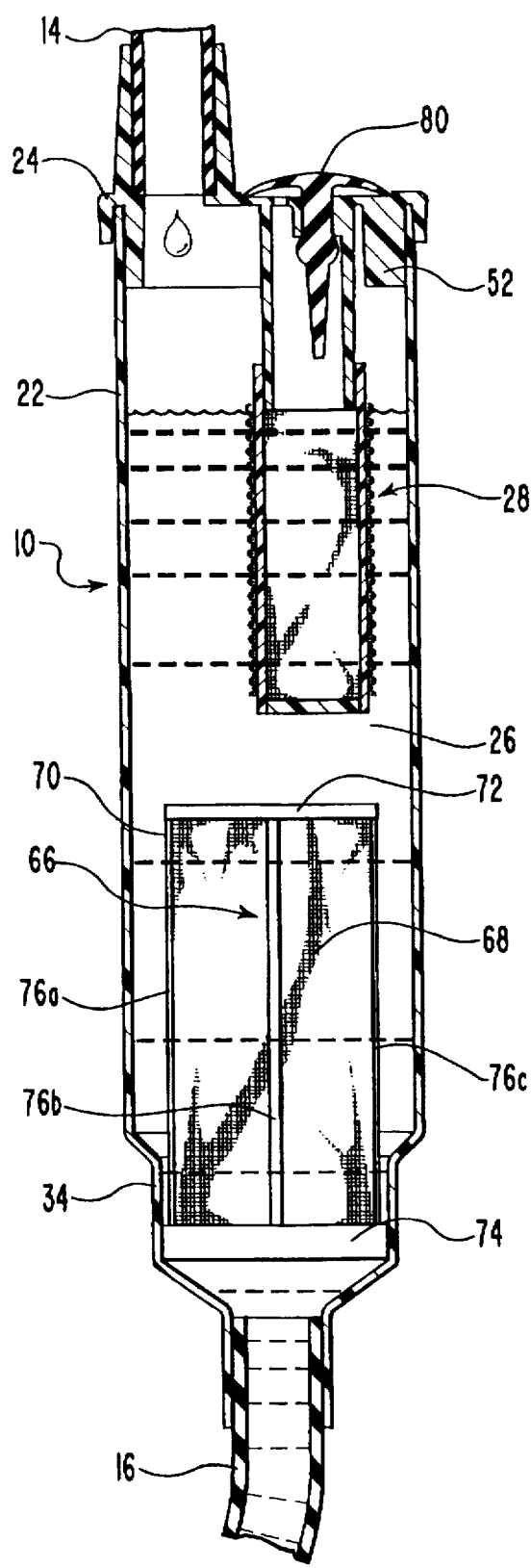
FIG. 4 is a cross sectional view depicting a fluid gas removal chamber with the hydrophobic membrane located below the fluid inlet to provide an air head space and allow for fluid flow rate monitoring.

Drip chamber 10 may optionally be provided with a means for filtering fluid prior to its passage through the outlet of drip chamber 10. In one presently preferred embodiment of the invention, the filtering means comprises a hydrophilic membrane assembly 66, disposed within interior chamber 26 at the distal end of drip chamber 10. As illustrated in FIG. 4, one embodiment of hydrophilic membrane assembly 66 comprises a hydrophilic membrane 68 and a support structure 70. In one presently preferred embodiment of hydrophilic filter assembly 66, support structure 70 comprises a circular end cap 72 situated at the proximal end of hydrophilic membrane 68, an annular base 74 situated at the distal end of hydrophilic membrane 68, and support ribs 76a-c integrally attached to, and extending between, circular end cap 72 and annular base 74. Hydrophilic membrane 68 permits the passage of fluid therethrough, but inhibits the passage of air bubbles and other contaminants that may be carried in the fluid. As illustrated in FIG. 4, annular base 74 is configured to mate within intermediate portion 34 of housing 22. Annular base 74 is securely and permanently fastened to the interior wall of intermediate portion 34 through the use of a suitable adhesive.

Figure 5:
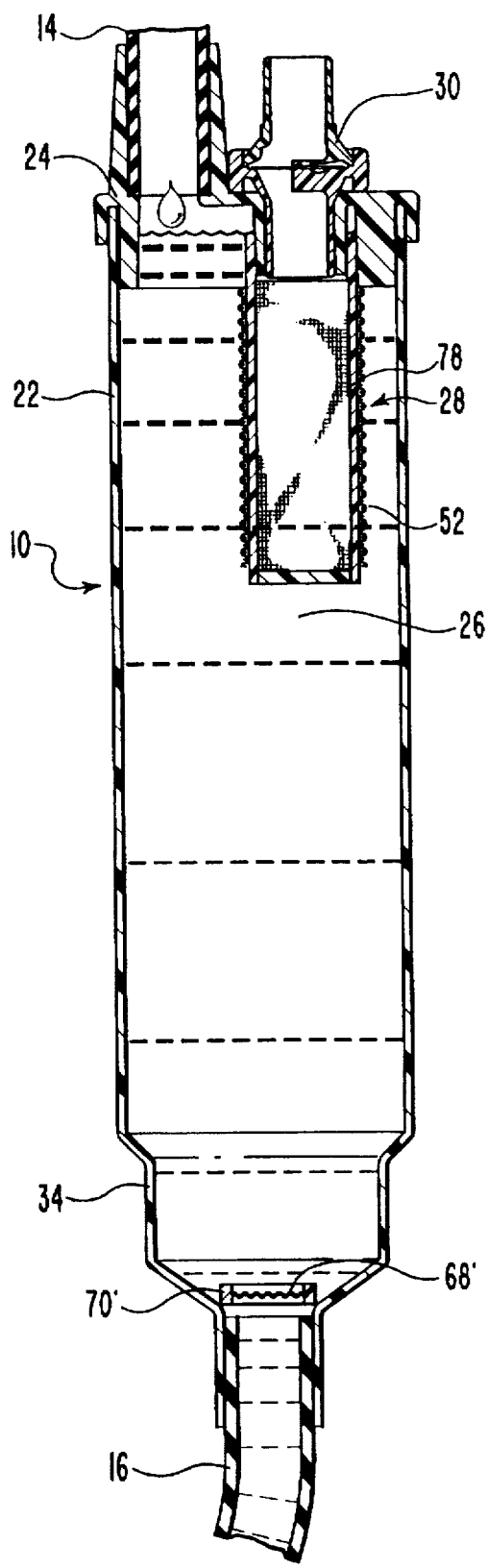
FIG. 5 is a cross sectional view of another embodiment of a fluid gas removal device within the scope of the present invention.

An alternative embodiment of hydrophilic filter assembly 66 is illustrated in FIG. 5. In this embodiment, hydrophilic filter assembly 66 simply comprises a supporting annular ring 70' and a flat, circular shaped hydrophilic membrane 68' securely fastened about its peripheral edge to ring 70'. Hydrophilic filter assembly 66 is only used for certain applications, such as for blood and intravenous systems, and is not used in situations or applications where filtration is provided at another location or for irrigation applications.

Drip chamber 10 is configured to be used with its longitudinal axis oriented in a generally vertical direction. In this orientation, drip chamber 10 presents an elongated, vertically oriented hydrophobic filter assembly 28, which has a relatively large membrane surface area. As discussed in more detail below, the vertical orientation of hydrophobic membrane assembly 28, coupled with its large surface area, produces superior performance in terms of longer service life and other benefits. As used herein, the "vertical orientation" of hydrophobic membrane is intended to include an angled membrane, but not an entirely horizontal hydrophobic membrane.

FIG. 7 illustrates another embodiment within the scope of the present invention which is designed for manufacturing simplicity. It includes two molded caps 24 and 94 which can be bonded to the tubular housing 22. Unlike the tubular housing 22 shown in FIG. 2, the tubular housing 22 shown in FIG. 7 can be cut to length from commercially available tubing. The various components can be quickly assembled and bonded to together to form the completed fluid gas removal chamber.

The use and operation of drip chamber 10 will now be described with reference generally to FIGS. 4 and 5. Fluid is introduced into the interior chamber 26 of drip chamber 10 through inlet line 14 from media bag 12. During the initial filling of interior chamber 26, air initially situated within interior chamber 26 is gradually displaced by the entering fluid, and is vented to the atmosphere through hydrophobic member 52 and check valve 30.

As drip chamber 10 is filled, the fluid level will initially rise to a point that is approximately even with the proximal or top end of hydrophobic membrane 52. At that point, the air occupying the space between the proximal end of hydrophobic member 52 and the distal end of inlet tube 14 will be trapped within interior chamber 26 and the hydrophobic membrane 52 will be completely blocked by the surrounding fluid.

If the top end of the hydrophobic membrane 52 is sufficiently below the distal end of inlet tube 14, a head space will exist at the proximal end of interior chamber 26 that permits visual monitoring of the rate at which fluid is flowing into drip chamber 10. Preferably, inlet tube 14 is terminated in such a manner that droplets are formed at the end of inlet tube 14 as they enter interior chamber 26. By visually monitoring the rate at which droplets form and enter interior chamber 26, a health care professional can approximate the rate at which fluid is being introduced into drip chamber 10.

As discussed above, it is common for air bubbles to be entrained within fluids introduced into interior chamber 26 of the fluid. As the fluid settles in interior chamber 26, any air introduced into interior chamber 26 tends to migrate the top surface of the fluid. As more and more air collects above the meniscus, the air collected at the top of interior chamber 26 forces the fluid level down to the point where a portion of hydrophobic membrane 52 is exposed to the trapped air. At that point, a portion of the air passes through hydrophobic membrane 52 and is vented to the atmosphere through check valve 30, umbrella valve 80, or similar venting device. Thus, drip chamber 10 has a self-regulating fluid level which rises and falls to the extent necessary to vent excess gas trapped in the upper portion of interior chamber 26 to the atmosphere.

Another feature of drip chamber 10 is that it automatically adjusts the rate at which gases can flow through hydrophobic membrane 52 upon the introduction of a large amount of air into interior chamber 26. During normal operation and use of drip chamber 10, a relatively small surface area of hydrophobic membrane 52 is exposed to the air trapped at the top of interior chamber 26. However, upon the introduction of a large volume of air and other gases into interior chamber 26, that large volume of air or other gas collects at the top of interior chamber 26, forcing the level of the fluid down and exposing a larger surface area of hydrophobic membrane 52 to the air or other gases. The increased surface area exposed to the gases effectively increases the overall flow rate through hydrophobic membrane 52.

In summary, the novel fluid gas removal device of the present invention overcomes several significant disadvantages of those found in the prior art. Specifically, the present invention provides a fluid gas removal device that allows the flow rate of fluid to be visually monitored and estimated by a health care professional without the need for a separate drip chamber. Moreover, the present invention provides a fluid gas removal device that minimizes the problems associated with occlusion of the hydrophobic filter. Further still, the present invention provides a fluid gas removal device that responds to increased inflow of gas by automatically increasing the flow rate through the hydrophobic filter.

The present invention may be embodied in other specific forms without departing from its essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by Patent is:

1. A fluid gas removal chamber for parenteral administration of fluids, comprising:
   a housing having an enclosed top end, and an outlet with an opening therethrough for discharge of fluid, said housing defining an interior chamber for receiving and collecting fluid;
   means for delivering fluid to said chamber;
   barrier means, disposed adjacent the top end and extending into said chamber, for establishing a vertically dimensioned hydrophobic barrier that will pass air from said chamber, without passing fluid; and
   vent means, in fluid communication with said barrier means, for venting air passed through the hydrophobic barrier of said barrier means.

2. The fluid gas removal chamber as recited in claim 1 wherein the barrier means comprises an elongate hydrophobic membrane, the elongate hydrophobic membrane comprising at least a portion of a three-dimensional surface.

3. The fluid gas removal chamber as recited in claim 2 wherein the barrier means further comprises means for supporting the hydrophobic membrane against collapse.

4. The fluid gas removal chamber as recited in claim 1, wherein the vent means further comprises means, in fluid communication with the vent means, for preventing air from entering the chamber through the vent means.

5. The fluid gas removal chamber as recited in claim 1 wherein the barrier means is disposed sufficiently below the top end such that in use, a void head space is formed which enables the monitoring of delivered fluid droplets.

6. The fluid gas removal chamber as recited in claim 5 wherein the means for delivering fluid to the chamber comprises a nozzle capable of forming the delivered fluid into droplets.

7. The fluid gas removal chamber as recited in claim 1 wherein the barrier means is disposed close to the top end such that in use, little or no void head space is formed between the top end and the delivered fluid.

8. The fluid gas removal chamber as recited in claim 1 further comprising means, disposed between the outlet and the means for delivering fluid, for filtering the fluid prior to passage through the outlet.

9. The fluid gas removal chamber as recited in claim 8 wherein the means for filtering the fluid comprises a hydrophilic barrier.

10. A fluid gas removal chamber for parenteral administration of fluids, comprising:

a housing having an enclosed top end, and an outlet with an opening therethrough for discharge of fluid, said housing defining an interior chamber for receiving and collecting fluid;

means for delivering fluid to said chamber;

barrier means, disposed adjacent the top end and extending into said chamber, for establishing an elongate hydrophobic barrier that will pass air from said chamber, without passing fluid;

vent means, in fluid communication with said barrier means, for venting air passed through the hydrophobic barrier of said barrier means; and means, in fluid communication with the vent means, for preventing air from entering the chamber through the vent means.

11. The fluid gas removal chamber as recited in claim 10 wherein the barrier means comprises means for supporting the elongate hydrophobic barrier against collapse.

12. The fluid gas removal chamber as recited in claim 10 wherein the barrier means is disposed sufficiently below the top end such that in use, a void head space is formed which enables the monitoring of delivered fluid droplets.

13. The fluid gas removal chamber as recited in claim 12 wherein the means for delivering fluid is constructed so as to be capable of forming the delivered fluid into droplets.

14. The fluid gas removal chamber as recited in claim 10 wherein the barrier means is disposed close to the top end such that in use, little or no void head space is formed between the top end and the delivered fluid.

15. The fluid gas removal chamber as recited in claim 10 comprising a cap which encloses the top end of the housing.

16. The fluid gas removal chamber as recited in claim 15 wherein the means for delivering fluid comprises a first passageway extending through the cap into the chamber.

17. The fluid gas removal chamber as recited in claim 16 wherein the vent means comprises a second passageway extending through the cap into the chamber.

18. The fluid gas removal chamber as recited in claim 17 comprising means, disposed between the outlet and the means for delivering fluid, for filtering the fluid prior to passage through the outlet.

19. The fluid gas removal chamber as recited in claim 18 wherein the means for filtering the fluid comprises a hydrophilic membrane.

20. The fluid gas removal chamber as recited in claim 19 wherein the hydrophilic membrane comprises at least a portion of a three-dimensional surface.

21. A fluid gas removal chamber for parenteral administration of fluids, comprising:

a housing having an enclosed top end, and an outlet with an opening therethrough for discharge of fluid, said housing defining an interior chamber for receiving and collecting fluid;

a cap enclosing the top end of the housing and having a first passageway and a second passageway formed therethrough;

means for delivering fluid to said chamber through the first passageway formed in the cap;

barrier means, in fluid communication with the second passageway formed in the cap and extending into said chamber, for establishing an elongate hydrophobic barrier that will pass air from said chamber, without passing fluid;

vent means, in fluid communication with said barrier means, for venting air passed through the hydrophobic barrier of said barrier means; and means, in fluid communication with the barrier means, for preventing air from entering the chamber through the vent means.

22. The fluid gas removal chamber as recited in claim 21 comprising means, disposed between the outlet and the means for delivering fluid, for preventing the passage of air through the outlet once fluid covers said means for preventing the passage of air.

* * * * *